US00PP34869P2

(12) United States Plant Patent
Clark et al.

(10) Patent No.: US PP34,869 P2
(45) Date of Patent: Dec. 27, 2022

(54) GRAPE PLANT NAMED 'DAZZLE'

(50) Latin Name: ***Vitis* L. hybrid**
Varietal Denomination: 'Dazzle'

(71) Applicant: THE BOARD OF TRUSTEES OF THE UNIVERSITY OF ARKANSAS, Little Rock, AR (US)

(72) Inventors: John R. Clark, Fayetteville, AR (US); Renee T. Threlfall, Springdale, AR (US); James N. Moore, Arlington, TX (US); Justin R. Morris, Springdale, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 17/532,200

(22) Filed: Nov. 22, 2021

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205, 206
CPC ..... A01H 5/08; A01H 5/0812; A01H 5/00; A01H 5/02; A01H 6/88; A01H 6/78
See application file for complete search history.

(56) References Cited

U.S. PATENT DOCUMENTS

PP6,159 P 4/1988 Reisch
PP30,425 P3 4/2019 Clark

OTHER PUBLICATIONS

Coneva et al. Investigations to Determine the Performance of Recently Released Seedless Table Grapes and Advanced Selections from the University of Arkansas Breeding Program, Hort Science 48(9) (Supplement) 2013 SR-ASHS Annual Meeding Feb. 2-5, 2013, S33-S34. (Year: 2013).*

Double A Vineyards, Dazzle, retrieved on Jan. 25, 2022, retrieved from the Internet at https://doubleavineyards.com/dazzle, 2 pp. (Year: 2022).*

Clark, J.R., et al. 2018. 'Opportunity' and 'Enchantment' wine grapes for the upper South of the United States. HortScience 53:1208-1211.

Mayfield, S. Winemaking potential for new Arkansas wine grapes. Presentation. Horticulture Industries Show. Tulsa, OK. Jan. 10, 2020. 33 pp.

McWhirt, A.L. et al. 2021. Small Fruit Cultivar Recommendations for Arkansas. University of Arkansas System Division of Agriculture. FSA6130. https://www.uaex.edu/publications/PDF/FSA-6130.pdf, 8 pp.

Threlfall, R.T., et al. "'Indulgence' and 'Dazzle': Two New White Wine Grapes for the US Mid-South." HortScience 57.3 (2022): 453-457.

Threlfall, R. T., et al. 2019. Evaluating Winemaking Potential for University of Arkansas Wine Grape Cultivars and Selections. HortScience 54(9) (Supplement 2)—2019 SR-ASHS Annual Meeting. P. S382.

Threlfall, R.T. et al. 2020. Introduction to the Arkansas Quality Wine Program. Arkansas Association of Grape Growers Virtual Conference. Nov. 5, 2020. Schedule. 1 page.

* cited by examiner

*Primary Examiner* — June Hwu
(74) *Attorney, Agent, or Firm* — Quarles & Brady LLP

(57) ABSTRACT

Description and specifications of a new and distinct cultivar of grapevine which originated from a hand-pollinated cross of 'Gewürztraminer' (female parent) x 'Melody' (male parent) made in 1991. The seedlings fruited in the summer of 1992 in a vineyard near Clarksville, Ark. and one was selected for its potential as a wine grape for utilization in the Mid-South of the United States. The original vine was tested as 'Ark. 2574'. The new cultivar of grapevine is intended for wine production and provides advancements in cold hardiness.

2 Drawing Sheets

Latin name: *Vitis* L. hybrid.
Varietal denomination: 'Dazzle'.

BACKGROUND

The new and distinct cultivar of grapevine named 'Dazzle' is described herein. The new cultivar originated from a hand-pollinated cross of 'Gewürztraminer' (not patented) x 'Melody' (U.S. Plant Pat. No. 6,159) made in 1991. The seedlings fruited in the summer of 1995 in a vineyard near Clarksville, Ark. and one was selected for its potential as a wine grape for utilization in the Mid-South of the United States. The original vine was tested as 'Ark. 2574'. The new cultivar is a pink-skinned (white) wine grape which provides advancement in cold hardiness as well as a light, fruity flavor in wine produced from the grapes.

SUMMARY OF THE INVENTION

The new and distinct cultivar of grapevine originated from a hand-pollinated cross of 'Gewürztraminer' (not patented) x 'Melody' (U.S. Plant Pat. No. 6,159) made in 1991 near Clarksville, Ark. The seeds resulting from this controlled hybridization were germinated in a greenhouse during the winter of 1991-92. Resulting seedlings were planted in the spring of 1992 in a vineyard near Clarksville, Ark. The seedlings fruited in the summer of 1995 and one seedling, designated Arkansas Selection 2574, was selected for its potential for processing and market production as a wine grape.

During late 1995 and early 1996, the original plant selection was propagated asexually at the above-noted location, by rooting hardwood cuttings. A test planting of three vines was established. In all propagations, hardwood cuttings were used and the selection rooted readily from hardwood cuttings. All propagules (resulting plants) of the new cultivar have been observed to be true to type in that during all asexual multiplication, the vegetative and fruit characteristics of the original plant have been maintained. All vines planted from hardwood cutting propagation fruited in the third season of growth in the vineyard after planting.

Vines of the new cultivar have good growth, not being excessively vigorous and good health as exhibited by good leaf color and limited disease presence. It has produced well as own-rooted plants in all testing and has not been evaluated on any rootstocks. Adaptation to the Arkansas test site is very good as winter injury or heat damage were minimal.

The health of the new cultivar is good. Vines were evaluated for presence of the following diseases and found to be moderately resistant to powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopara viticola* Berl. & de Toni.), but were not tested for resistance to anthrancnose (*Elsinoë ampelina* Shear), and black rot (*Guignardia bidwellii* Viala & Ravaz). Fungal diseases can be fully controlled by the use of available fungicides.

The new cultivar average harvest date is 15 August in Clarksville, Ark. The berries are small (ca. 1.9 g) and globose in shape. Fruit is seeded. The flavor of the grape is light and semi-fruity and soluble solids averaged 19.4%. Fruit cracking and skin splitting has not been observed in severe rainfall pressure seasons. Clusters are medium, with compact cluster-fill. Average cluster weight is 162.3 g in Arkansas. Yield averages 9.8 kg/vine in Arkansas.

The flavor attributes for the new cultivar are reflective of commercial standards for quality juice and wine. Wine of the new cultivar is comparable to white wine hybrids and *V. vinifera*. Soluble solids and titratable acidity concentration of the juice at crush averages 19.9% and 0.70% respectively. Juice pH averages 3.27. The crush juice yield is 6.5 kg of grapes for 3.8 L of juice.

The new cultivar has been named 'Dazzle'.

BRIEF DESCRIPTION OF THE PHOTOGRAPHS

The accompanying photographs show typical specimens of the new cultivar in color as nearly true as it is reasonably possible to make in a color illustration of this character. The data collection was from vines that were 23 years old.

DETAILED DESCRIPTION OF THE NEW CULTIVAR

Figure 1:
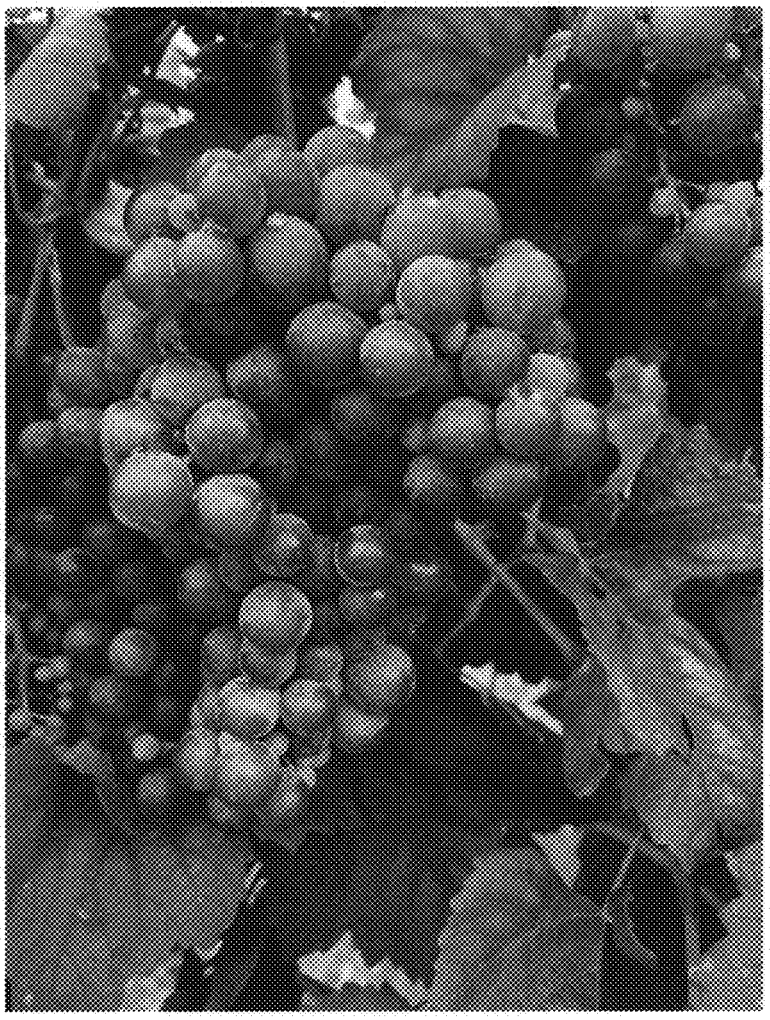
FIG. 1 is a photograph showing typical cluster of healthy fruit, near Clarksville, Ark.
Figure 2:
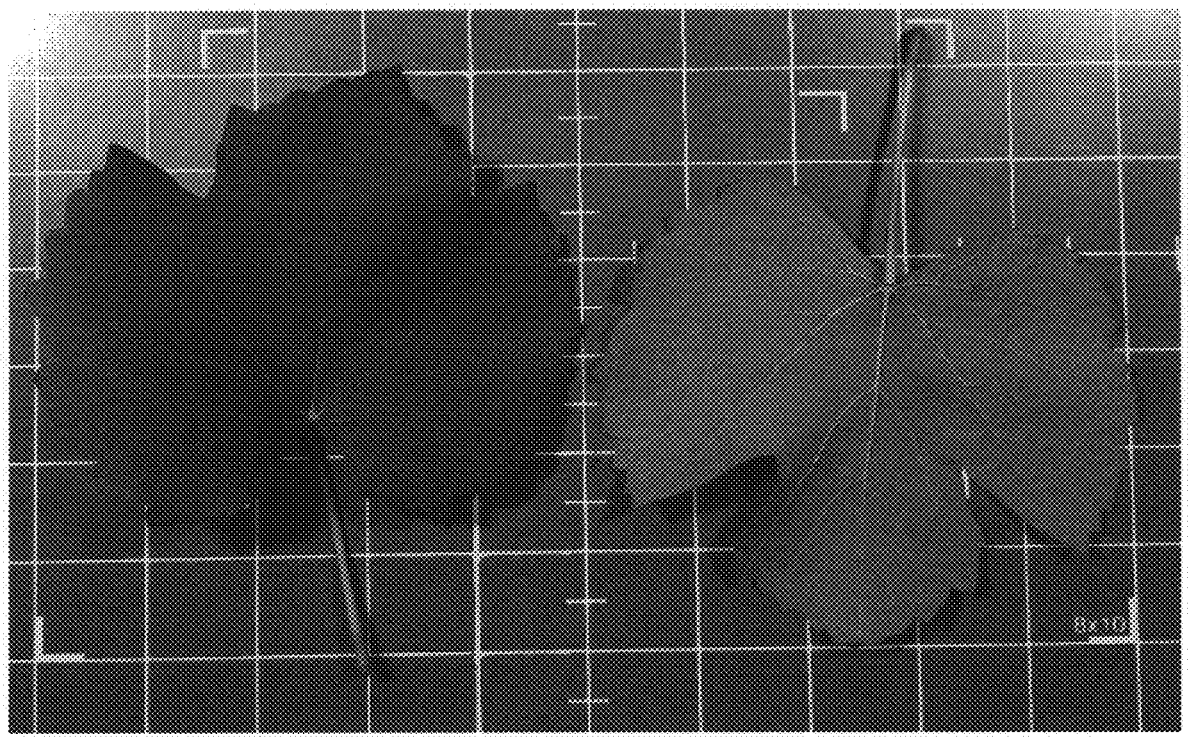
FIG. 2 is a photograph showing the leaf abaxial view (right) and adaxial view (left), near Clarksville, Ark.

'Dazzle' differs from its female parent, 'Gewürztraminer', in that it ripens earlier in the season. 'Dazzle' differs from its white-skinned male parent, 'Melody', in that the fruit skin color is pink on 'Dazzle'. The soluble solids content of 'Dazzle' averages 19.4%, in contrast to 18.6% average soluble solid content of 'Melody'. Average yield of 'Dazzle' (9.8 kg/vine) is similar to that of 'Melody' (9.7 kg/vine). 'Dazzle' is distinctly different from similar varieties of grapevines currently cultivated. The proposed variety has higher soluble solids than 'Opportunity' (U.S. Plant Pat. No. 30,425) which averages 17.3%. Ripe berries are 1 g smaller than 'Opportunity'.

The following is a detailed description of the botanical and pomological characteristics of the subject grapevine. Color data are presented in Royal Horticultural Society Colour Chart designations, 1986 version, second edition.

Where dimensions, sizes, colors and other characteristics are given, it is to be understood that such characteristics are approximations of averages set forth as accurately as practicable.

The descriptions reported herein are from specimens grown near Clarksville, Ark. Vines used for measurement were irrigated using trickle (drip) irrigation. Vines were fertilized annually in spring with Nitrogen or complete fertilizers. No shoot or leaf thinning practices were conducted on the vines.

Vine:

*Size*.—Evaluation vines are grown on a 1.5 m tall, single-wire trellis, bilateral cordon training system spaced 2.4 m between vines. Vines occupy this space fully.

*Growth vigor*.—Moderate, not excessive.

*Density of foliage*.—Heavy.

*Productivity*.—9.8 kg/vine.

*Rootstock*.—None; own-root.

*Cold hardiness*.—Hardy to −26° C. (−15° F.); potentially hardier as this was the coldest temperature experienced at the test site.

Shoots (current-season canes):

*Color of shoots* (*current-season canes*).—Sun-exposed surface: greyed-orange group 177A; shaded surface: yellow-green group 144A; anthocyanin present: yes; anthocyanin color; greyed-purple group 186A.

*Shoot attitude*.—Shoots hang downward (procumbent).

*Openness of shoot tip*.—Half open.

*Prostrate hairs on young shoot tip*.—Medium to dense.

Canes (mature, dormant):

*Color of mature, dormant cane*.—Base: greyed-orange group 177B uniformly; midpoint: greyed-orange group 166B uniformly; terminal: yellow-green group 144B with greyed-orange group 166B overtones of anthocyanin on sun-exposed portions.

*Texture of mature, dormant canes*.—Smooth.

*Shape of dormant cane*.—Round.

*Length of mature, dormant canes*.—130.46 cm.

*Diameter of mature, dormant cane*.—Base: 0.78 cm; midpoint: 0.58 cm; terminal: 0.36 cm.

*Internode length of mature, dormant canes*.—Base: 3.66 cm; midpoint: 6.85 cm; terminal: 2.59 cm.

*Lenticels*.—Not present.

*Maturity in the fall*.—Canes were mature to tips in the fall.

Trunk:

*Diameter at* 30 *cm above soil level*.—1.27 cm.

*Shape*.—Angular.

*Trunk straps*.—Present.

*Surface texture*.—Rough, with peeling bark.

*Color*.—Inner bark color: greyed-orange group 177B; outer bark color: grey group 201B.

Foliage:

*Arrangement of mature leaves*.—Alternate.

*Shape of mature leaves*.—Lobed.

*Number of lobes on mature leaves*.—2 lobes.

*Petiole sinus of mature leaves*.—Wide open; depth: 3.20 cm; width: 3.29 cm.

*Venation of mature leaves*.—Pinnate.

*Margin of mature leaves*.—Serrate.

*Teeth shape of mature leaves*.—Serrate, both sides straight to both sides convex.

*Size of teeth*.—Depth: 3.87 mm; width: 7.65 mm.

*Surface texture of mature leaves*.—Abaxial surface: smooth, no blistering; adaxial surface: smooth, no blistering.

*Dimensions of mature leaves*.—Length: 9.70 cm; width: 13.68 cm; thickness: 0.04 cm.

*Pubescence on mature leaves*.—Abaxial surface: none; adaxial surface: moderate; prostrate hairs between main veins: medium to dense; amount of erect hairs on main veins: sparse.

*Color of mature leaves*.—Base abaxial: yellow-green group 146B; base adaxial: green group 137A; midpoint abaxial: yellow-green group 146B; midpoint adaxial: green group 137A; terminal abaxial: yellow-green group 146B; terminal adaxial: green group 137B; no anthocyanin on any portion of leaves.

*Color of veins on mature leaves*.—Abaxial surface: yellow-green group 146D; adaxial surface: yellow-green group 144A; no anthocyanin on any portion of leaf veins.

*Autumn coloration of mature leaves*.—Abaxial surface: yellow-orange group 18B; adaxial surface: yellow-orange group 18A.

*Leaf pubescence on young leaves*.—Abaxial surface: none; adaxial surface: heavy.

*Color of young leaves*.—Base abaxial: yellow-green group 146C; base adaxial: yellow-green group 144A; midpoint abaxial: yellow-green group 146C; midpoint adaxial: yellow-green group 144A; terminal abaxial: yellow-green group 146C; terminal adaxial: yellow-green group 144A; no anthocyanin present on young leaves.

*Vein color of young leaves*.—Abaxial surface: yellow-green group 145D; adaxial surface: yellow-green group 145D.

*Texture of young leaf veins*.—Abaxial surface: smooth; adaxial surface: heavy pubescence.

Petioles:

*Color of mature petioles*.—Yellow-green group 146C.

*Anthocyanin present, mature petioles*.—Yes; color: orange-red group 31C.

*Dimensions of mature petioles*.—Length: 7.43 cm; diameter: 0.28 cm.

*Color of young petioles*.—Green group 142B.

*Anthocyanin present, young petioles*.—Yes; color: orange-red group 31A.

*Dimensions of young petioles*.—Length: 11.70 mm; diameter: 1.22 mm.

Tendrils:

*First tendril found at node number*.—6.

*Orientation*.—Opposite.

*Dimensions*.—Length 11.05 cm: diameter: 1.98 mm.

*Texture*.—Smooth, no pubescence.

*Color of mature tendril*.—Yellow green group 145A.

*Shape and tendency*.—Tendrils are forked and curled.

Buds:

*Number of buds on current, single-season cane*.—22.

*Dimensions of dormant buds*.—Width: 4.90 mm; length: 4.08 mm.

*Shape of dormant buds*.—Triangular with rounded corners.

*Color of dormant buds*.—Greyed-orange group 175C.

*Texture of dormant buds*.—Smooth, no pubescence on scales.

*Bud break*.—2 April, medium.

Disease resistance: Vines were evaluated for presence of the following diseases and found to be moderately resistant to powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopara viticola* Berl. & de Toni.), but were not tested for resistance to anthrancnose (*Elsinoë ampelina* Shear), and black rot (*Guignardia bidwelhi* Viala & Ravaz). Fungal diseases can be fully controlled by the use of available fungicides.

Flower:

*Fragrance*.—Moderate, sweet.

*Sex*.—Hermaphrodite.

*Bloom dates*.—First bloom: May 15; full bloom: May 18; last bloom: 21 May.

*Flowers per cluster*.—234.

*Inflorescence dimensions*.—Length: 8.73 cm; diameter: 5.15 cm.

*Flower dimensions*.—Length: 3.03 mm; diameter: 5.82 mm.

*Flower longevity*.—<7 days, flowers senesce quickly and transition to fruit development.

*Flower shape*.—Round; with calyptra, inconspicuous.

Stamens:

*Number*.—5.

*Color*.—Filament: yellow-green group 145C; anther: yellow-green group 153D.

Pistil:

*Number*.—1.

*Length*.—2.37 mm.

*Color*.—Yellow-green group 144B.

Pollen:

*Color*.—Yellow-green group 153D.

*Quantity*.—Moderate.

Petal:

*Number*.—5.

*Color*.—Yellow-green group 144A.

Sepal: None.

Pedicel:

*Dimensions*.—Length: 0.52 cm; diameter: 0.12 cm.

*Color*.—Yellow-green group 144B.

Fruit:

*Maturity*.—15 August.

*Berry shape overall*.—Globose.

*Berry shape in cross-section*.—Round/circular.

*Berry color*.—Skin: greyed-orange group 177A, moderate waxy bloom present; flesh: greyed-green group 195A; anthocyanins: absent from flesh.

*Berry dimensions*.—Diameter at equator: 1.29 cm; diameter at base: 0.30 cm; diameter at apex: 0.54 cm; length: 1.35 cm.

*Berry weight*.—1.5 g.

*Berry skin texture*.—Non-slip skin, firm.

*Firmness*.—Soft, 4.99 N of pressure required to compress the berry 5 mm. A Stable Micro Systems TA.XT.Plus Texture Analyzer (Texture Technologies Corporation, Hamilton, Mass.) was used. Fruit compression was performed by placing 5 individual berries on a flat surface using a cylindrical plane probe of 7.6 cm diameter at a rate of 2 $mm \cdot s^{-1}$ with a trigger force of 0.02 N. The probe traveled 5 mm after first contact, and the peak force (N) was recorded as berry firmness.

*Skin thickness.*—0.03 cm.
*Tenacity.*—Moderate.
*Brush length.*—0.33 cm.
*Seeds.*—Present.
*Number of seeds per berry.*—2, fully developed/inedible.
*Seed size.*—Length: 6.92 mm; width: 3.92 mm; weight: 46 mg.
*Seed color.*—Greyed-orange group 176B.
*Juiciness.*—High, very juicy.
*Flavor.*—Light, neutral, herbaceous.

Juice:
*Soluble solids.*—19.4%.
*Titratable acidity.*—0.71 g/L tartaric acid.
*ph.*—3.26.
*Color.*—Yellow-green group 149D.

Cluster:
*Weight.*—162.3 g.
*Cluster dimensions.*—Length: 12.98 cm; width: 7.16 cm.
*Berries per cluster.*—140.
*Clusters per vine.*—182.
*Clusters per shoot.*—2.
*Peduncle (primary).*—Length: 3.55 cm; diameter: 0.20 cm; color: yellow-green group 144C.
*Density.*—Compact.

Use: Processing for white wine production with improved vines particularly adapted for Arkansas and the Mid-South of the United States.

We claim:

1. A new and distinct cultivar of grape plant named 'Dazzle', substantially as illustrated and described.

* * * * *